United States Patent
Mombrun et al.

(10) Patent No.: US 10,886,117 B2
(45) Date of Patent: Jan. 5, 2021

(54) METHOD OF SPATIALIZED FREEING AND CAPTURING OF BIOLOGICAL SPECIES USING A TISSUE PLACED ON A FUNCTIONALIZED SUPPORT

(71) Applicant: COMMISSARIAT A L'ENERGIE ATOMIQUE ET AUX ENERGIES ALTERNATIVES, Paris (FR)

(72) Inventors: Adrien Mombrun, Grenoble (FR); Mohamed-Ali Bouamrani, Grenoble (FR); Celine Le Clec'h, Teche (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 21 days.

(21) Appl. No.: 16/473,975

(22) PCT Filed: Dec. 13, 2017

(86) PCT No.: PCT/FR2017/053545
§ 371 (c)(1),
(2) Date: Jun. 26, 2019

(87) PCT Pub. No.: WO2018/122487
PCT Pub. Date: Jul. 5, 2018

(65) Prior Publication Data
US 2020/0321206 A1  Oct. 8, 2020

(30) Foreign Application Priority Data
Dec. 29, 2016 (FR) .................................. 16 63528

(51) Int. Cl.
*H01J 49/04* (2006.01)
*G01N 1/28* (2006.01)
(Continued)

(52) U.S. Cl.
CPC ............ *H01J 49/0418* (2013.01); *G01N 1/28* (2013.01); *G01N 1/405* (2013.01); *G01N 33/6851* (2013.01); *G01N 2560/00* (2013.01)

(58) Field of Classification Search
None
See application file for complete search history.

(56) References Cited

U.S. PATENT DOCUMENTS

| | | | | |
|---|---|---|---|---|
| 2007/0278400 | A1* | 12/2007 | Schurenberg | G01N 1/4055 250/288 |
| 2014/0377793 | A1* | 12/2014 | Bouamrani | A61B 10/02 435/29 |
| 2015/0093780 | A1* | 4/2015 | Schurenberg | G01N 1/4055 435/40.52 |

FOREIGN PATENT DOCUMENTS

| | | |
|---|---|---|
| GB | 2 437 623 A | 10/2007 |
| GB | 2437623 A * | 10/2007 |

(Continued)

OTHER PUBLICATIONS

International Search Report dated Mar. 23, 2018 in PCT/FR2017/053545 filed Dec. 13, 2017.

*Primary Examiner* — Andrew Smyth
(74) *Attorney, Agent, or Firm* — Oblon, McClelland, Maier & Neustadt, L.L.P.

(57) ABSTRACT

The invention is a method for capturing biological species present in a body tissue. The method comprises an arrangement of tissue on a support, referred to as a capture support, capable of selectively capturing one or more biological species, referred to as species of interest. The method comprises; —a step of depositing a lysis reagent on the tissue; —a step of droplet formation, on the surface of the tissue, each droplet comprising the solubilized lysis reagent; —a formation of lysis sites, in the tissue, between each droplet and the capture support, such that at each lysis site, (Continued)

species of interest are freed and captured by the capture support.

12 Claims, 6 Drawing Sheets

(51) Int. Cl.
  *G01N 33/68* (2006.01)
  *G01N 1/40* (2006.01)

(56) References Cited

FOREIGN PATENT DOCUMENTS

WO    WO 2013/098703 A1    7/2013
WO    WO-2013098703 A1 *    7/2013 ............. A61B 10/02

* cited by examiner

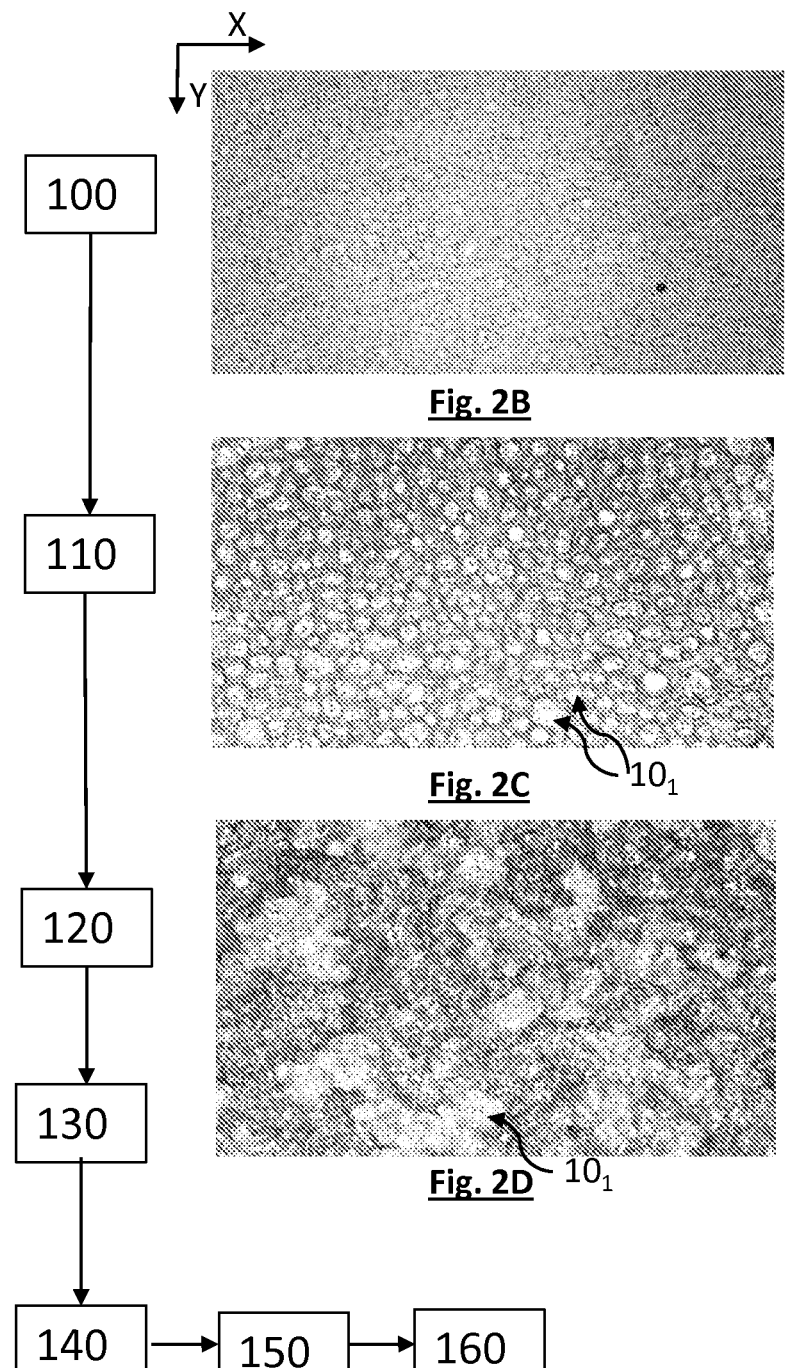

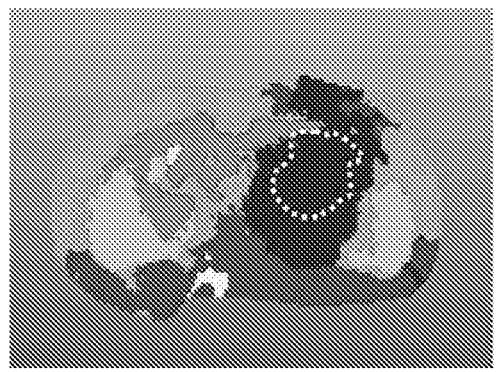
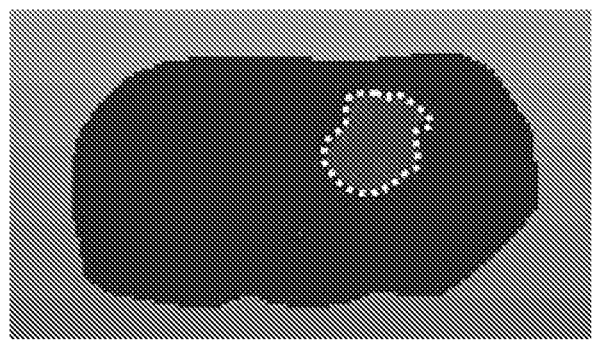
Fig. 6A      Fig. 6B
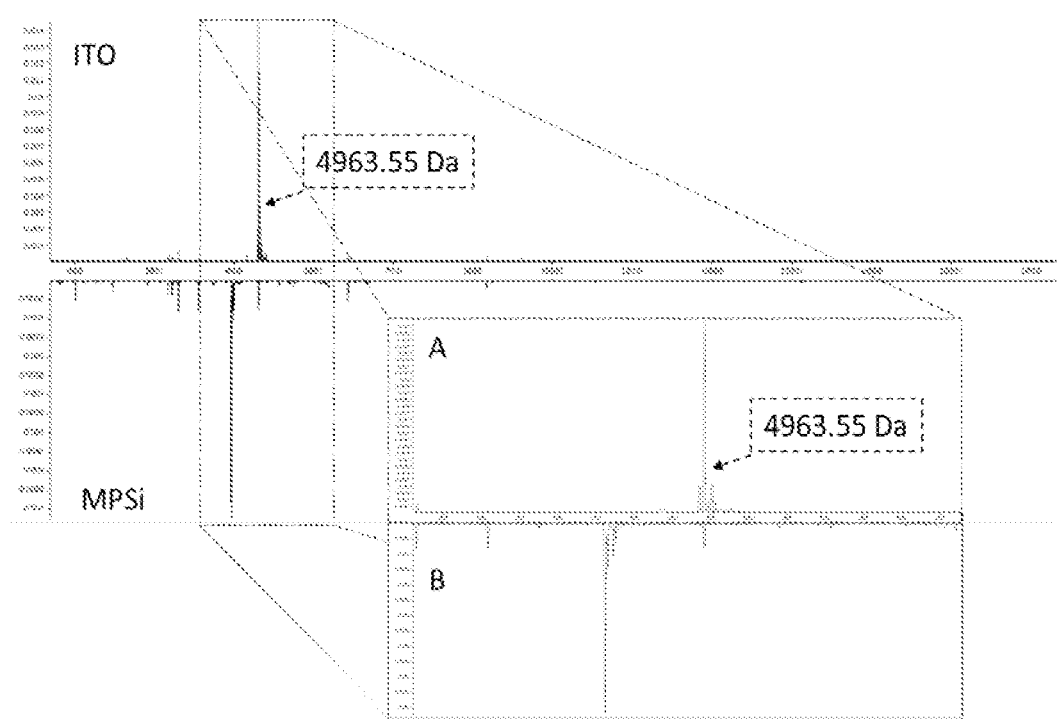
Fig. 7

METHOD OF SPATIALIZED FREEING AND CAPTURING OF BIOLOGICAL SPECIES USING A TISSUE PLACED ON A FUNCTIONALIZED SUPPORT

TECHNICAL FIELD

The technical field of the invention is the spatialized and selective release and capture of biological species, for example proteins or peptides, from a tissue, for example a histological tissue section, deposited on a functionalized support, for example made of nanoporous silicon.

PRIOR ART

Histological or immunohistochemical analysis in anatomopathology consists in analyzing samples of biological tissue of small thickness in order to establish a diagnosis. The tissue sample is generally in the form of a thin section, obtained according to known preparation methods, from a specimen taken by exeresis, biopsy or smear. The preparation consists in forming a section of fine thickness deposited on a support, generally a transparent support. Before cutting, the tissue can be frozen as it is or chemically fixed, dehydrated and embedded in a paraffin matrix. The histological analysis of the tissue section is carried out routinely using histological dyes, conventionally hematoxylin and eosin, so as to determine the topography of the tissue. The section can also be analyzed by immunohistochemistry, which uses antibodies targeted on proteins known to be biomarkers of a given pathological condition so as to refine the clinical diagnosis. However, these techniques are subject to the practitioner's assessment, the specificity/sensitivity of the antibodies, and the relevance of the biomarkers chosen. They can prove to be insufficient and irrelevant for an objective and specific diagnosis of a given pathological condition, and are unsuitable for the search for new biomarkers for clinical diagnosis.

Recently, molecular imaging by mass spectrometry, and in particular MALDI-TOF (Matrix Assisted Laser Desorption Ionization-Time of Flight) imaging, has emerged as a new alternative for unsupervised molecular analysis of histological sections of biological tissues. It makes it possible to semi-quantitatively determine the spatial distribution of organic and/or inorganic molecules (for example: metabolites, peptides, proteins, lipids, pharmaceutical molecules). However, the sensitivity of the technique is limited by the presence of predominant and abundant molecules, not relevant to diagnosis, the search for biomarkers, or the detection of a specific molecule. In particular, the concentration range and the number of molecules present in a biological sample cause a loss of sensitivity of the analysis for the detection of potentially advantageous molecules, that is to say biomarkers. It is therefore necessary to fractionate the sample, in such a way as to decomplexify it, and thus to improve the sensitivity of the detection, and also the number of molecules detected on one and the same sample.

Application WO 2013/098703 describes a capture support made of nanoporous silicon, intended to be placed on a tissue. Due to its porosity, the support makes it possible to selectively sample low-molecular-weight proteins, the latter binding in the pores. After rinsing, the proteins sampled remain confined in the pores, whereas the large proteins are eliminated. Since the support is conductive, it is compatible with molecular imaging by MALDI mass spectrometry, so as to obtain a spatial distribution of the molecules of interest. Such a support thus constitutes a particularly promising tool for the spatialized enrichment of low-molecular-weight molecules of a biological tissue. Furthermore, the performance qualities of MALDI mass spectrometers (sensitivity, spectral resolution) are optimal below 20 000 Da, that is to say for the low molecular weights. The method thus described allows better detection sensitivity and also a greater number of molecules detected, each having the potential to be a relevant marker for the given pathological condition.

The inventors of the present invention have used a capture support similar to the one described in this application WO 2013/098703. They have developed a method of analysis that is particularly suitable for histological tissue sections. The method makes it possible to carry out an effective analysis of tissue sections, and constitutes an attractive alternative to the methods normally used in histological analyses.

SUMMARY OF THE INVENTION

A subject of the invention is a method for capturing biological species from a biological tissue, comprising the following steps:
  a) application of a biological tissue onto a capture support, the capture support being capable of selectively capturing at least one biological species, referred to as the biological species of interest;
  b) deposition of a lysis reagent onto the biological tissue;
  c) bringing of the lysis reagent thus deposited into contact with a solvent, so as to form droplets, spaced out from one another, at the surface of the tissue, the droplets comprising the lysis reagent solubilized by the solvent;
  d) formation of lysis sites, each lysis site corresponding to a portion of the tissue extending between a droplet and the captured support and, in each lysis site, lysis of the tissue by the lysis reagent solubilized by the solvent, the lysis bringing about a release and then a capture of the biological species of interest of the tissue by the capture support;
  e) rinsing of the capture support, in order to remove the uncaptured biological species.

The method may also comprise a step f) of spatially resolved analysis of the nanoporous support, so as to obtain spatial information relating to the biological species captured during step d). The analysis carried out is generally spatially resolved mass spectrometry, for example laser desorption mass spectrometry.

According to one embodiment, during step b), the lysis reagent may be sprayed onto the tissue. According to one embodiment, during step b), the lysis reagent condenses on the tissue, so as to form solid deposits, or crystals, on said tissue. According to this embodiment, the method may comprise a sublimation of the lysis reagent, such that the lysis reagent, in the gaseous state, condenses on the tissue.

According to one embodiment, during step c), the droplets are formed by condensation of the solvent on the tissue. According to another embodiment, during step c), the droplets are formed by spraying the solvent onto the tissue.

The capture support may be a nanoporous support, preferably comprising pores of which the diameter or the largest size is less than 1 μm. The capture support may be made of silicon. It may be a capture support functionalized by deposition of a layer capable of retaining biological species of interest.

The tissue is preferably arranged according to a section. The tissue thickness may be less than 50 μm or 20 μm.

Other advantages and features will emerge more clearly from the following description of particular embodiments of the invention, given by way of nonlimiting example, and represented in the figures listed below.

FIGURES

FIGS. 1A, 1B, 1C and 1D represent various phases of a method according to the invention.

FIG. 2A represents schematically the principal steps of a method according to the invention. FIG. 2B represents a view under a microscope of a crude tissue section prior to implementing the method. FIG. 2C represents a view under a microscope of a tissue section after obtaining "spatialized" lysis, according to an embodiment in which the lysis reagent is sublimated and condensed on the tissue, then in which lysis is activated by incubation in a chamber saturated with solvent vapors. FIG. 2D represents a view under a microscope of a tissue section after obtaining spatialized lysis according to a variant according to which the lysis reagent is sprayed onto the tissue, in liquid form, then lysis is activated by spraying a solvent.

FIGS. 6A and 6B are examples of hierarchical spatial segmentation of a spectral image by considering respectively a slide of tissue deposited on a reference support and a tissue deposited on a nanoporous support.

FIG. 7 shows a comparison of a spectrum obtained respectively with a slide of tissue deposited on a reference support and a tissue deposited on a nanoporous support.

SUMMARY OF PARTICULAR EMBODIMENTS

Figure 1A:
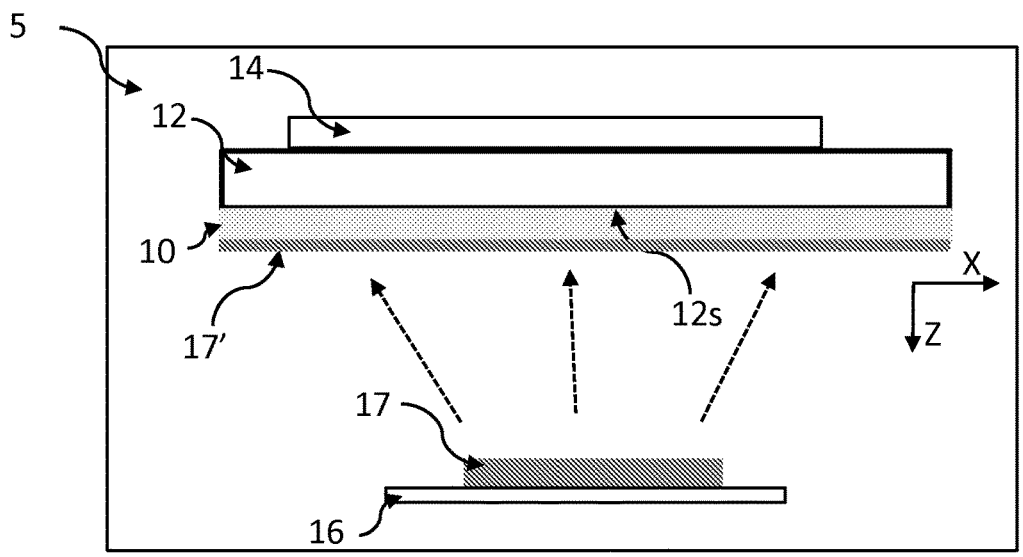
Figure 1B:
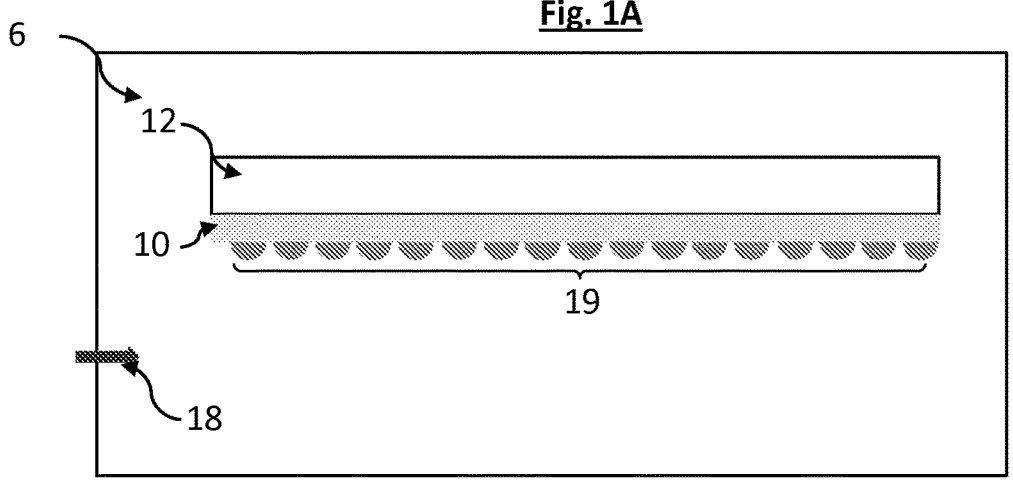

Represented in FIG. 1A is a slide of body tissue 10, deposited on the surface 12s of a nanoporous support 12, the assembly being maintained in a chamber 5. The thickness of the slide of tissue is preferably less than 50 μm, and is in particular between 4 μm and 20 μm. It is a conventional histological section, obtained from a frozen tissue or from a tissue fixed in paraffin.

The nanoporous support consists of pores, of which the diameter, or the largest dimension, parallel to the surface 12s of the support is between 1 nm and 100 nm. The porosity is greater than 10%, and is preferably between 30% and 80% depending on a thickness extending, from the surface 12s, between 10 nm and 100 μm, or even further. The porosity denotes the volume occupied by the pores relative to the volume of the support in the depth in question. The support may be a porous silicon support, as described in application WO 2013/098703, or any other support having a functionalized surface and enabling the capture of biological species, for example by chemical functionalization.

The surface 12s may be porous, functionalized and porous, or functionalized and non-porous. The term "functionalized" is understood to mean a surface having undergone a surface treatment, so as to have an affinity with respect to a biological species of interest in such a way as to capture it. The term "biological species" denotes a species present in a biological tissue, and released from the tissue following lysis of said tissue. It may in particular be an endogenous species, for example a protein or a peptide, an exosome or other molecule naturally present in the tissue. It may also be an exogenous biological species, for example a molecule forming a therapeutic agent, or a marker, it being possible for the marker to be organic or inorganic. In general, the biological species that are of interest to the invention have a size (diameter or large dimension) or are inscribed in a diameter of less than a few nanometers, for example less than 10 nm or 20 nm.

The surface functionalization methods are known: these involve for example depositing a function layer which allows selective capture of certain species. The functional layer may be a chemical layer, comprising for example a C-18 material, conducive to the capture of peptides and small proteins, or an anionic or cationic layer. It may also be a layer which enables selective capture by antigen-antibody grafting.

The surface 12s extends along a plane XY, the dimensions in this plane being for example 7.5×2.5 cm, which corresponds to the dimensions of a standard-format microscope slide.

The nanoporous support may be mesoporous, which usually denotes pores of which the diameter is between 2 nm and 50 nm. In general, the term "nanoporous" denotes a material, preferably of uniform composition, having pores of which the mean diameter is less than 1 μm (1 micrometer), and usually less than 100 nm. The mesoporous materials have the dimensions which correspond best to the intended applications, that is to say the capture of small proteins or of peptides.

In the experimental examples described below, the nanoporous support is obtained from a boron-doped silicon substrate 100, of diameter 200 mm, having been the subject of electrochemical anodization in a hydrofluoric acid solution (HF). The electrolyte used during the anodization comprises 3 volumes of HF, 3 volumes of isopropanol (IPA) and 4 volumes of water. The resistivity of silicon is between 10 and 20 mΩ·cm$^{-1}$. The mean diameter of the pores is 15 nm, and they extend to a depth of 1 μm. This is a mesoporous support.

Other methods for producing a nanoporous support can be envisioned, for example an electron-beam lithography method.

The nanoporous support 12 is deposited against a cooler 14, so as to maintain the support 12 and, by thermal conduction, the tissue 10, at a temperature of less than the ambient temperature of the chamber 5. The temperature of the support may for example be about 0° C. to 4° C. The cooler 14, or cold generator, may be a thermoelectric generator, for example a Peltier-effect generator, a thermoregulated fluidic circuit or a cold finger connected to a cryostat. Maintaining the support 12 at low temperature promotes condensation effects described below.

The chamber 5 also comprises a radiator 16, on which is placed a lysis reagent 17 in the solid state, for example in the form of a powder. The pressure in the chamber is adjusted such that, under the effect of an increase in the temperature of the radiator 16, the lysis reagent is sublimated. The sublimation of the lysis reagent 17 is represented, in FIG. 1A, by dashed arrows.

A portion of the sublimated lysis reagent comes into contact with the tissue 10, maintained at low temperature by the support 12. As a result, there is solid condensation, or crystallization, of the lysis reagent 17 on the tissue 10. The crystallization forms fine crystals 17' distributed relatively homogeneously over the surface of the tissue. The size of these crystals is also relatively uniform, and may be for example in the region of 100 nm. A relatively homogeneous dry deposit is thus formed at the surface of the tissue 10.

The lysis reagent 17 may be urea, or may comprise predominantly urea, the reagent being deposited on the radiator 16 in the form of a powder. When the pressure inside the chamber is $2 \times 10^{-3}$ mbar, and the radiator is brought to a temperature of between 90° C. and 120° C., the urea is sublimated in the chamber.

Urea constitutes the preferred lysis reagent, the inventors having observed optimal results with lysis reagent, but other lysis reagents can be envisioned, for example detergents, of Triton (registered trade mark) X-100 $((C_{14}H_{22}O(C_2H_4O)_n))$ or Tween (registered trade mark) −20-type, zwitterionic active agents (HEPES-4-(2-hydroxyethyl)-1-piperazineethanesulfonic acid) or enzymes.

After deposition of the lysis reagent on the tissue 10, the support 12 is placed in a chamber 6, the atmosphere of which is rich, or even saturated, with a solvent 18 in the vapor phase. The choice of the solvent depends on the lysis reagent 17 previously used. When the lysis reagent 17 is urea, the solvent 18 may be an aqueous solution of ammonium bicarbonate (50 mM), or an aqueous solution comprising methanol (for example 30% by volume of methanol-70% by volume of water). It may also be a solution of methanol with an ammonium bicarbonate concentration of 50 mM. The ambient temperature of the chamber 6 is brought to between 30° C. and 95° C., so as to increase the amount of solvent 18 present in the vapor phase. The solvent in the vapor phase condenses at the surface of the tissue 10, forming droplets 19 of solubilized lysis reagent on said surface. The diameter of each droplet 19 is preferably less than 50 μm, and is preferably less than 20 μm. It may in particular be between 5 μm and 20 μm. The droplets are preferably spaced out from one another. The lysis reagent crystals are solubilized by the droplets 19 condensed on the tissue 10. Each droplet 19 thus constitutes a microreservoir of solubilized lysis reagent. In order to promote the condensation of the solvent 18, the cooling of the support 12 may be maintained.

Figure 1C:
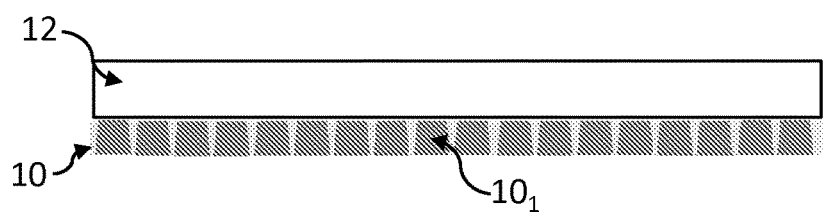

The condensation of the solvent is controlled so that the droplets 19 of solubilized lysis reagent are not too large, so as to prevent adjacent droplets 19 from coalescing. The parameters controlling the formation and the size of the solvent droplets 19 are in particular the temperature in the chamber, the temperature of the tissue and also the duration of the exposure of the tissue to the solvent. These parameters are adjusted so as to obtain droplets 19 of preferentially less than 50 μm in size, separated from one another, while at the same time being sufficiently close to one another. Specifically, at each elementary droplet 19, the lysis reagent 17 is solubilized and impregnates the tissue 10, as illustrated in connection with FIG. 1C. Thus, at each droplet 19, the tissue undergoes localized lysis. Each elementary droplet 19 brings about the formation of a lysis site $10_1$, in which the tissue is lyzed. In each lysis site $10_1$, the biological material present in the tissue is released, and can meet the surface 12s of the nanoporous support 12. The support 12 acts as a capture support with regard to certain biological species, referred to as biological species of interest, the latter being retained at the level of the pores of the support 12.

The distribution of the droplets 19 at the surface of the tissue leads to a similar distribution of the lysis sites in the tissue, each lysis site being separated from one another. Each lysis site $10_1$ extends between each droplet 19 and capture support 12. Two adjacent lysis sites are separated by tissue $10_2$ referred to as residual, comprising non-lyzed tissue or tissue lyzed to a lesser extent than at a lysis site $10_1$. An important point of the invention is that of obtaining a two-dimensional distribution of the lysis sites $10_1$ along a plane XY according to which the tissue section extends, and having a sufficient spatial resolution. Preferably, the distribution of the lysis sites is as regular as possible. A regular distribution is obtained when the droplets 19 formed at the surface of the tissue are regularly spaced out and have substantially the same size. The term "substantially the same size" is understood to mean the same size, a tolerance of +1-50% being accepted.

Figure 1D:
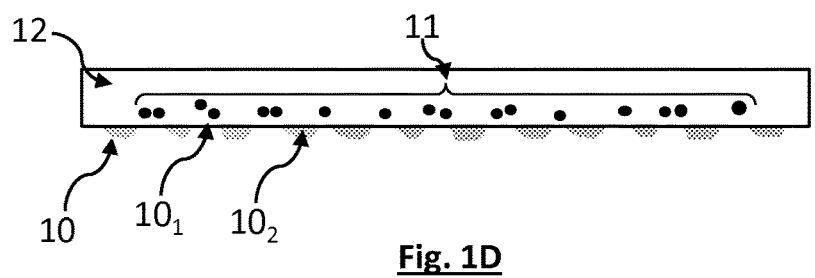

The distribution of the lysis sites $10_1$ in the tissue 10 makes it possible to obtain lysis referred to as spatialized, according to the spatial distribution of each droplet 19 of solvent previously deposited at the surface of the tissue. This spatialization of the lysis leads to a spatialized capture of biological species of interest, at each lysis site. Indeed, under the effect of the lysis, biological species 11 are released by the tissue at each lysis site $10_1$. They are channeled by the residual parts $10_2$, and migrate toward the capture support 12, as illustrated in FIG. 1D.

The support 12 is then rinsed, so as to remove the uncaptured biological species. After rinsing, the support 12 may be the subject of a spatially resolved analysis, so as to characterize the captured biological species. As previously indicated, the size of each lysis site $10_1$ depends on the size of the droplets 19 previously described. The inventors have estimated that the size of the droplets may be between 5 and 50 μm. The larger the droplets 19, the more effective the lysis, which promotes the sensitivity of the measurement, to the detriment of the spatial resolution. When the droplets 19 are small in size, for example between 5 and 15 μm, the spatial resolution is optimal, but the sensitivity of the measurement is reduced. The inventors consider that it is preferable for the size of the droplets 19 to be between 10 and 30 μm, so as to favor the spatial resolution.

Thus, a key point of the method is to allow a spatialized lysis, regarding a functionalized capture support which makes it possible to capture certain biological species, prior to a spatially resolved analysis. This makes it possible to trace back to a spatial distribution of the biological species 11 captured in the tissue 10. If the lysis was not spatialized, mixing could occur during the lysis process, and the information about localization, in the tissue, of the captured species would be lost.

The spatially resolved analysis of the sample can in particular be laser desorption mass spectrometry, for example of MALDI or SELDI (Surface Enhanced Laser Desorption Ionization) type.

FIG. 2A represents the main steps of the method, described in relation to FIGS. 2B, 2C and 2D, the latter being images of a slide of tissue observed under a microscope (optical magnification×10).

Step 100: placing of the tissue opposite the lysis reagent. FIG. 2B represents an image of a tissue section tested. It is a section, 10 µm thick, obtained from a specimen of a rat brain deep-frozen at −20° C. After cutting, the section is dried for 30 minutes, washed with ethanol (between 70% and 100% by volume) for 30 seconds, then dipped in a fixative (Carnoy's solution, known to those skilled in the art) for 2 minutes, then rinsed with ethanol.

Step 110: application of a lysis reagent 17 by sublimation of the lysis reagent and condensation on the tissue.

Step 120: solubilization of the lysis reagent. This involves bringing the lysis reagent 17, distributed at the surface of the tissue 10, into contact with a solvent 18, for example in the vapor phase. This step can also be referred to as "incubation".

Step 130: spatialized lysis of the tissue 10, leading to spatialized capture of biological species 11 by the capture support 12.

Step 140: rinsing of the surface 12s of the support 12, by three baths of distilled water for one minute each, so as to remove the residual parts of non-lyzed tissue. The inventors have observed that urea is removed very well by simple rinsing, unlike other lysis agents, the latter leaving traces that can generate a contamination of the molecular analysis by mass spectrometry.

The method can therefore comprise a treatment step 150 with a view to an analysis by laser desorption mass spectrometry. This involves depositing an organic matrix, for example by spraying. The method also comprises a step 160 of mass spectrometry analysis, so as to obtain a spatial distribution of mass spectra, and thus obtain spectral information representative of each elementary lyzed part $10_1$.

FIG. 2C is an image of a tissue section, similar to that represented in FIG. 2B, after implementation of steps 100 to 130, described above. Lysis sites $10_1$ distributed according to a two-dimensional meshing are observed at the surface of the tissue. The lysis sites correspond to the lightest parts of the image. Each lysis site $10_1$ is delimited by a residual part $10_2$, corresponding to the dark outlines.

According to one variant, during step 110, the deposition of the lysis reagent 17 on the tissue is not carried out by sublimation, but by spraying. This leads to the formation of droplets 17' on the tissue 10. The size of the droplets sprayed may be between 10 µm and 20 µm. An example of a lysis reagent is an aqueous solution of urea, with a molarity of between 4M and 8M. According to this variant, during step 120, the droplets of lysis reagents impregnate with solvent, forming droplets 19 of solubilized lysis reagent.

According to another variant, during step 120, the solvent 18 is applied to the tissue by being sprayed, so as to form droplets 19 with a diameter preferentially less than 50 µm at the surface of the tissue.

FIG. 2D represents an image of a tissue, similar to that represented in FIG. 2B, after spraying of the lysis reagent, then spraying of the solvent in the vapor phase. The light parts correspond to lysis sites $10_1$. This image was obtained with the same magnification as FIG. 2C. The lysis sites are larger and less clearly delimited than on the image 2C.

The inventors have noted that the deposition of the lysis reagent by spraying makes it possible to obtain a better lysis efficiency, resulting in an increase in sensitivity, whereas a deposition of lysis reagent by sublimation makes it possible to obtain a better spatial resolution. This is due to the fact that sublimation allows the formation of droplets 19 that are smaller than those obtained by spraying.

Experimental Tests

Experimental tests were carried out on slides of rat brain 10 µm thick as described above. The brain sample comprised two tumor zones. The tests were carried out taking into consideration, on the one hand, a nanoporous support (denoted by the acronym MPSi) and, on the other hand, an ITO (indium tin oxide) support, forming a reference support. The tissues deposited on each slide are comparable, and are from the same specimen. The tissues were the subject of a MALDI-TOF (Time of Flight) mass spectrometry analysis in linear mode with an acceleration voltage of +20 kV using an Ultraflex III MALDI TOF/TOF device (Bruker Daltonics) equipped with a laser operating according to a pulse frequency of 1000 Hz. The spectra were acquired according to a mass/charge ratio range of between 1000 and 20 000 Da (Daltons). The lateral resolution is 75 µm, with 300 laser impacts per point. Prior to the acquisition of the spectra, the samples were covered with an organic matrix, applied by spraying. The matrix used is a mixture of methanol/water/trifluoroacetic acid, with respective volume fractions of 50/49.8/0.2. The spectra discussed below are standardized by the total ion current, that is to say all of the channels of the spectrum.

Figure 3:
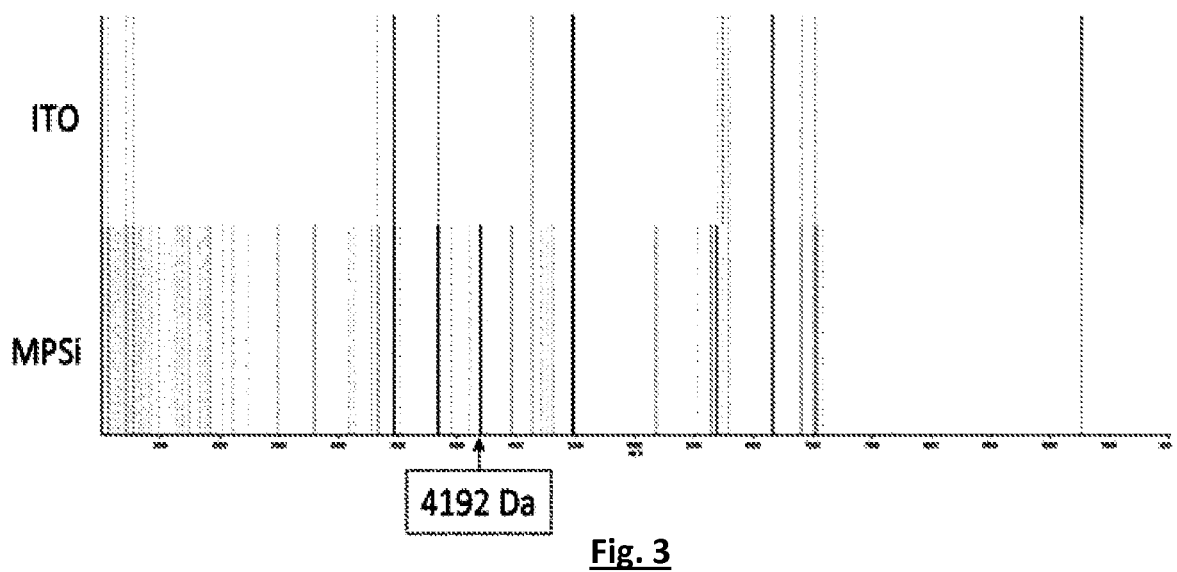
FIG. 3 shows a spectrum acquired by carrying out the method described in connection with FIG. 2A respectively on a smooth support of indium tin oxide used as reference support, and on a nanoporous silicon support.

FIG. 3 represents a spectrum, a spectral band of between 1000 and 20 000 Da, acquired with a reference support (ITO), prepared according to a standard method, and also by implementing the invention, on a nanoporous silicon (MPSi) capture support. It is observed that the spectrum acquired using the nanoporous support comprises more peaks: the spectral information is thus richer, and capable of revealing traces not detectable with the conventional ITO support.

Figure 4A:
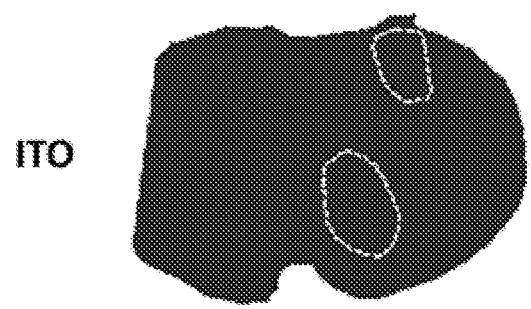
FIGS. 4A and 4B represent respectively a spatial distribution of the intensity of a peak corresponding to a mass of 4192 Da, resulting from mass spectra obtained on a slide of tissue deposited on a reference support and on a nanoporous support.
Figure 4B:
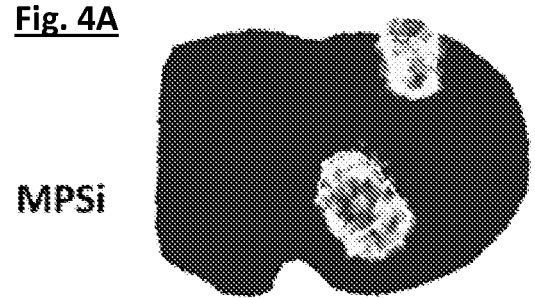

FIGS. 4A and 4B represent, for each point of the tissue (each point representing a pixel of 75 µm of 75 µm), the intensity of the peak of 4192 Da. FIG. 4A corresponds to the ITO support, while FIG. 4B corresponds to the nanoporous support. FIG. 4A comprises a signal comparable to background, while FIG. 4B makes it possible to localize the presence of this peak in the tumor zones delimited by dashed lines. Such a peak can thus correspond to a spectral signature of a tumor, that can be clearly observed by means of the invention.

Figure 5A:
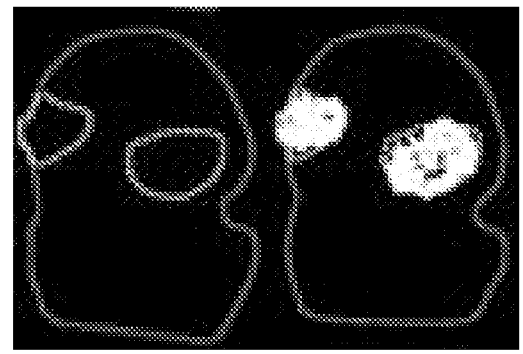
FIG. 5A represents a spatial distribution of the intensity of a peak corresponding to a mass of 4207 Da resulting from mass spectra obtained on a slide of tissue deposited on a reference support and on a nanoporous support.

FIG. 5A represents a spectral image produced at 4207 Da, with the ITO support on the right and the nanoporous support on the left. It is once again observed that the invention makes it possible to obtain more information specific to the tumor.

Figure 5B:
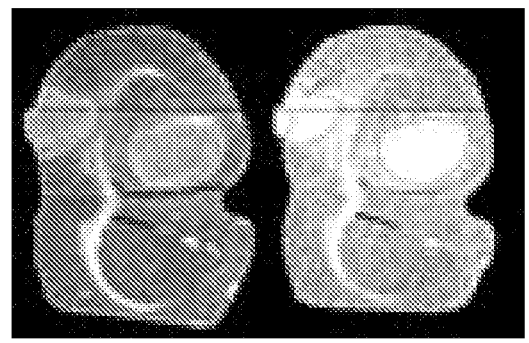
FIG. 5B represents an image, produced with a scanner, of a slide of tissue deposited on a reference support and on a nanoporous support.

FIG. 5B represents optical images of the tissues, produced using a scanner, the spectral images of which were represented in FIGS. 4A, 4B and 5A. The left-hand part of the image represents the tissue deposited on an ITO support. The right-hand part of the image represents the tissue deposited on the nanoporous silicon support. The anatomy of the skull and the presence of tumors are clearly observed.

Figure 5C:
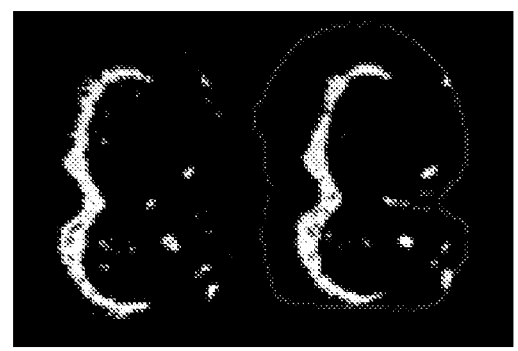
FIG. 5C represents a spatial distribution of the intensity of a peak corresponding to a mass of 7080 Da resulting from mass spectra obtained on a slide of tissue deposited on a reference support and on a nanoporous support.

FIG. 5C represents spectral images produced at 7080 Da, with the ITO support (left-hand part) and the nanoporous support (right-hand part). The peak at 7080 Da makes it possible to observe the corpus callosum on each image. FIG. 5C makes it possible to verify the coherence of the results obtained with the two supports on a known reference spectral band.

FIGS. 6A and 6B show an example of hierarchical spectral classification carried out respectively with the ITO support and the nanoporous support. This classification makes it possible to group together the various spatial zones at the level of which similar spectra were acquired. Thus, the tissue examined is divided into various spatial zones, as a function of a spectrum similarity criterion. The classification can be carried out iteratively, so as to obtain a classification representative of the anatomical characteristics of the tissue examined. In FIG. 6A, several classes of spectra have been defined. The outlines of the tumor appear in an approximate manner. This classification required five successive iterations. In FIG. 6B, the classification algorithm determined two classes, one corresponding to the healthy portion, the other corresponding to the tumor portion. This classification was obtained in a single iteration. The invention makes it possible to obtain a better discrimination between a spectrum acquired in a tumor zone and a spectrum acquired in a healthy zone.

FIG. 7 represents the average spectrum representing the average of all the spectra acquired on the entire brain histological section, respectively with an ITO support and a nanoporous support (MPSi), the two supports having undergone the same treatment protocol. It is observed that the average spectrum obtained with the nanoporous support comprises a peak at 4963.55 Da, corresponding to the Thymosin Beta-4 peptide, greatly decreased compared with the average spectrum obtained with the nanoporous support 12. It is an abundant peptide, the presence of which can mask the detection of small proteins or other peptides. Its reduction on the spectrum obtained with the nanoporous support is thus advantageous. Parts A and B of the figure correspond to zooms of the spectra respectively acquired using the ITO support and the nanoporous support, the zoom corresponding to a region of spectral interest at around 4963.55 Da.

Figure 8:
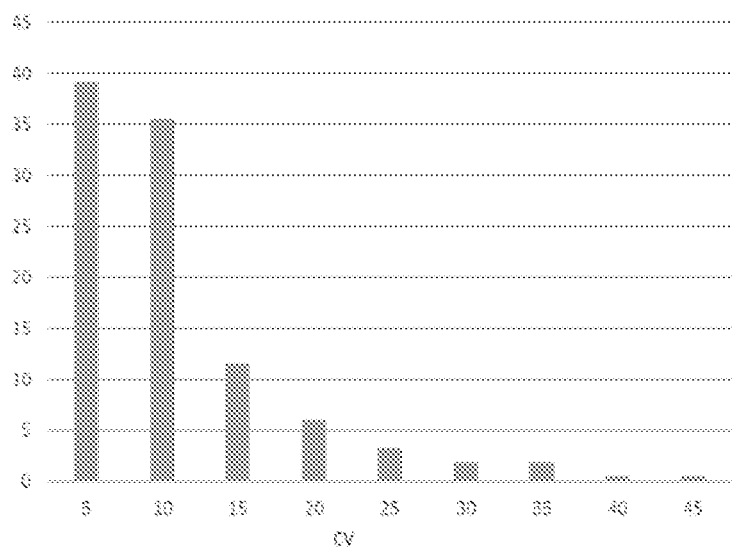
FIG. 8 represents a histogram of the coefficients of variation of the peaks detected on three consecutive analyses of sections taken from one and the same sample.

The reproducibility of the method was tested. Three sections corresponding to the same specimen were deposited on a similar nanoporous silicon support, and were the subject of a preparation and a spectral analysis as described above. An average spectrum was measured on each section, the three average spectra obtained comprising 350 peaks in common. The coefficient of variation of intensity of each peak was calculated on the three average spectra. FIG. 8 represents a histogram of the coefficients of variation CV. The abscissa represents the value of a coefficient of variation, and the ordinate represents the number of peaks. It is observed that 90% of the peaks detected on the three sections have a coefficient of variation of less than 15%. These results attest to a good reproducibility of the method.

The invention may be carried out as an aid to diagnosis or as a research tool, so as to determine specific tracers for particular pathological conditions.

The invention claimed is:

1. A method for capturing biological species from a biological tissue, comprising:
   a) applying a biological tissue onto a capture support, the capture support configured to selectively capture at least one biological species of interest;
   b) depositing a lysis reagent onto the biological tissue;
   c) bringing the lysis reagent thus deposited into contact with a solvent, so as to form droplets, spaced out from one another, at the surface of the biological tissue, the droplets comprising the lysis reagent solubilized in the solvent;
   d) forming lysis sites, each lysis site corresponding to a portion of the biological tissue extending between a droplet and the capture support and, in each lysis site, lysing the biological tissue by the lysis reagent solubilized by the solvent, the lysis bringing about a release of the biological species of interest from the biological tissue and then a capture of biological species of interest of the tissue by the capture support; and
   e) rinsing the capture support, in order to remove the uncaptured biological species.

2. The method of claim 1, wherein the method further comprises:
   f) carrying out a spatially resolved analysis of the capture support, so as to obtain information relating to the spatial distribution of the biological species of interest captured during d).

3. The method of claim 2, wherein, during f), the analysis carried out is spatially resolved mass spectrometry.

4. The method of claim 1, wherein, during b), the lysis reagent is sprayed onto the biological tissue.

5. The method of claim 1, wherein, during b), the lysis reagent condenses on the biological tissue, so as to form one or more solid deposits on said tissue.

6. The method of claim 5, comprising a sublimation of the lysis reagent such that the lysis reagent, in the gaseous state, condenses on the biological tissue.

7. The method as of claim 1, wherein, during c), the droplets are formed by condensation of the solvent on the tissue.

8. The method of claim 1, wherein, during c), the droplets are formed by spraying the solvent onto the tissue.

9. The method of claim 1, wherein the capture support is a nanoporous support, comprising pores of which the diameter or the largest size is less than 1 µm.

10. The method of claim 1, wherein the capture support is made of silicon.

11. The method of claim 1, wherein the thickness of the biological tissue is less than 50 µm.

12. The method of claim 1, wherein the thickness of the biological tissue is less than 20 µm.

* * * * *

UNITED STATES PATENT AND TRADEMARK OFFICE
CERTIFICATE OF CORRECTION

PATENT NO. : 10,886,117 B2  
APPLICATION NO. : 16/473975  
DATED : January 5, 2021  
INVENTOR(S) : Adrien Mombrun et al.

Page 1 of 1

It is certified that error appears in the above-identified patent and that said Letters Patent is hereby corrected as shown below:

On the Title Page

Column 1, Item (72), in "Inventors", Line 3, delete "Teche" and insert -- Têche --, therefor.

In the Claims

In Column 10, Claim 1, Line 13, delete "of the tissue by" and insert -- by --, therefor.

In Column 10, Claim 7, Line 33, delete "as of" and insert -- of --, therefor.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*